United States Patent [19]
Whipple

[11] Patent Number: 5,947,984
[45] Date of Patent: *Sep. 7, 1999

[54] ULTRASONIC CLAMP COAGULATOR APPARATUS HAVING FORCE LIMITING CLAMPING MECHANISM

[75] Inventor: Gary Whipple, South Attleboro, Mass.

[73] Assignee: Ethicon Endo-Surger, Inc., Cincinnati, Ohio

[21] Appl. No.: 08/949,133

[22] Filed: Oct. 10, 1997

[51] Int. Cl.$^6$ .................................................. A61B 17/32
[52] U.S. Cl. .............................................. 606/151; 601/2
[58] Field of Search ................................... 606/151, 152, 606/153, 154, 155, 156, 157, 158, 142, 143, 205, 206, 207, 169, 170, 171, 174; 227/901, 902

[56] References Cited

U.S. PATENT DOCUMENTS

| | | |
|---|---|---|
| 4,522,206 | 6/1985 | Whipple et al. . |
| 5,314,406 | 5/1994 | Arias et al. ................................ 604/21 |
| 5,322,055 | 6/1994 | Davison et al. ......................... 606/169 |
| 5,405,344 | 4/1995 | Williamson et al. .................... 606/143 |
| 5,411,481 | 5/1995 | Allen et al. .......................... 606/151 X |
| 5,653,721 | 8/1997 | Knodel et al. ........................... 606/151 |
| 5,681,330 | 10/1997 | Hughett et al. ...................... 606/151 X |

FOREIGN PATENT DOCUMENTS

| | | |
|---|---|---|
| 19534618 | 3/1997 | Germany . |
| 8-275948 | 10/1996 | Japan . |
| 8-275949 | 10/1996 | Japan . |
| 8-275951 | 10/1996 | Japan . |
| 9-98980 | 4/1997 | Japan . |

OTHER PUBLICATIONS

UltraCision Incorporated, Harmonic Scalpel Operating Manual, Ref. N Mar. 1995, 53 pages.
UltraCision Incorporated, Harmonic Scalpel Price List, Jul. 1995, 7 pages.
UltraCision Incorporated, The Harmonic Scalpel for Gynecological Surgery, 1993, 4 pages.
Ultracision CS/LS Layout, Jul. 24, 1995, 2 pages.
Snowden–Spencer, Inc., Endoscopic Plastic Surgery, 1993, 10 pages.

*Primary Examiner*—Michael Buiz
*Assistant Examiner*—Vickey Trinh

[57] ABSTRACT

An ultrasonic surgical clamp coagulator apparatus is configured to effect cutting, coagulation, and clamping of tissue by cooperation of a clamping mechanism of the apparatus with an associated ultrasonic end-effector. In order to limit the force with which tissue is clamped between a clamp arm of the clamping mechanism and the end-effector, the clamping mechanism includes a force-limiting spring which operatively connects an operating lever of the apparatus and components of the clamp drive mechanism. The force-limiting spring is preferably pre-loaded so that the interconnection of the associated components is desirably "stiff", thus providing a user with good tactile feedback during operation of the clamping mechanism. At least one travel stop is preferably provided on the apparatus housing for limiting movement of the operating lever after a predetermined degree of relative movement of the operating components in opposition to the force-limiting spring.

8 Claims, 7 Drawing Sheets

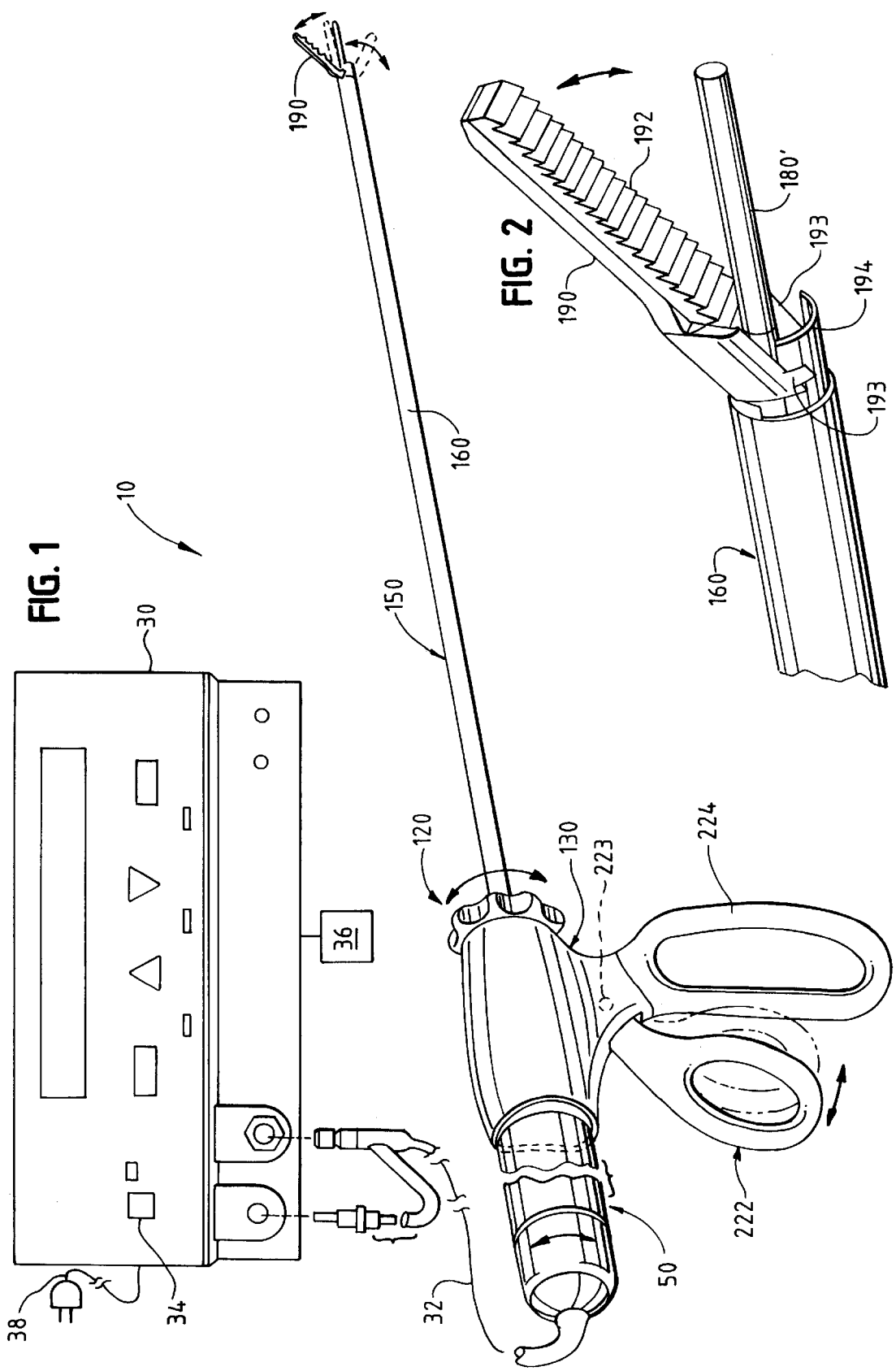

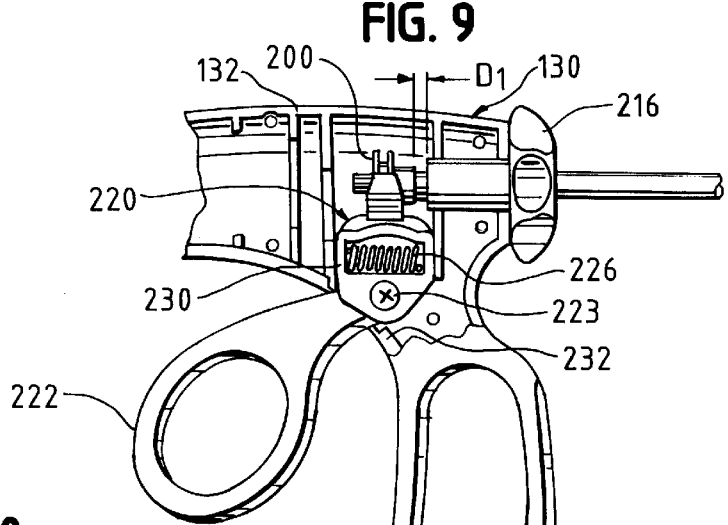
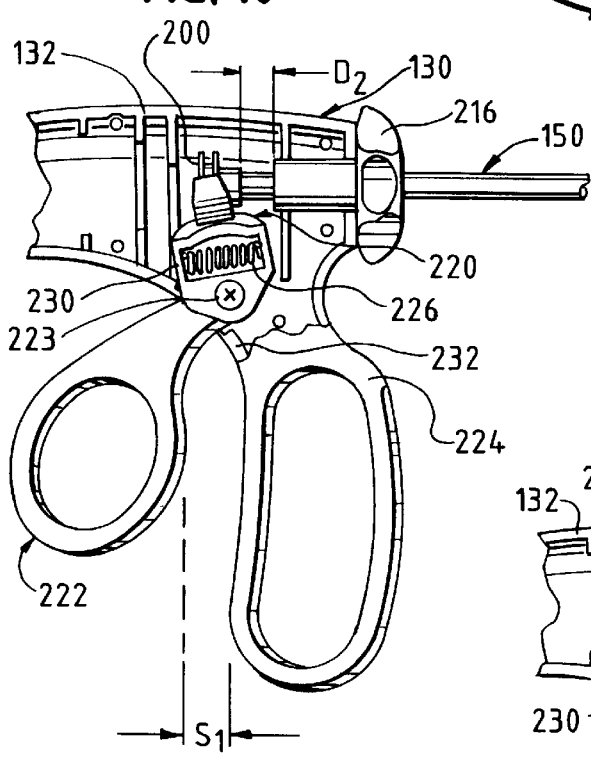
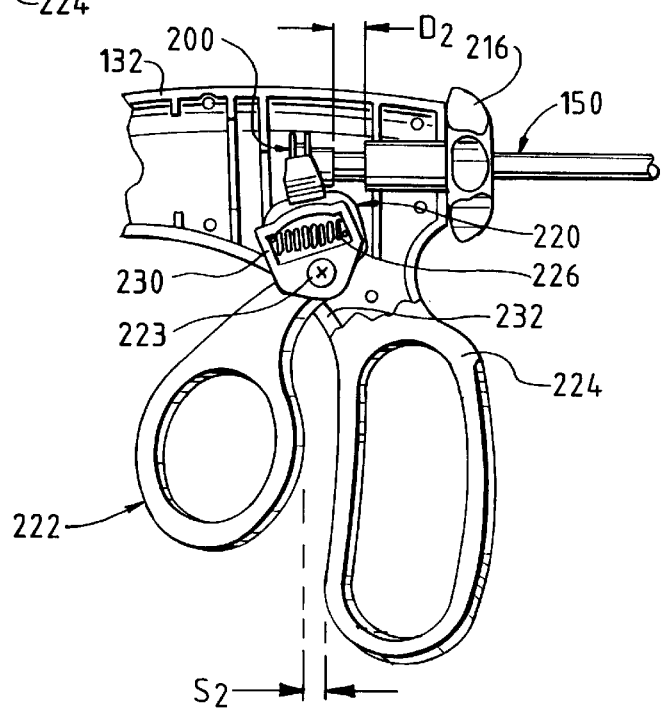

ULTRASONIC CLAMP COAGULATOR APPARATUS HAVING FORCE LIMITING CLAMPING MECHANISM

TECHNICAL FIELD

The present invention relates generally to ultrasonic surgical devices, and more particularly to an ultrasonic surgical clamp coagulator apparatus for coagulating and/or cutting tissue, including a clamping mechanism having an arrangement for preventing application of excessive clamping force to tissue gripped by the mechanism.

BACKGROUND OF THE INVENTION

Ultrasonic surgical instruments are finding increasingly widespread applications in surgical procedures by virtue of the unique performance characteristics of such instruments. Depending upon specific instrument configurations and operational parameters, ultrasonic surgical instruments can provide substantially simultaneous cutting of tissue and hemostasis by coagulation, desirably minimizing patient trauma. The cutting action is typically effected by an end-effector at the distal end of the instrument, with the end-effector transmitting ultrasonic energy to tissue brought into contact therewith. Ultrasonic instruments of this nature can be configured for open surgical use, or laparoscopic or endoscopic surgical procedures.

Ultrasonic surgical instruments have been developed that include a clamp mechanism to press tissue against the end-effector of the instrument in order to couple ultrasonic energy to the tissue of a patient. Such an arrangement (sometimes referred to as an ultrasonic transector) is disclosed in U.S. Pat. No. 5,322,055, hereby incorporated by reference.

One important design parameter in providing a ultrasonic clamp coagulator or similar apparatus is configuring the device to prevent application of excessive clamping force, while maintaining good tactile feedback for the user of the instrument. In some previous constructions, no specific mechanism has been provided for limiting clamping forces, with forces thereby typically limited only by flexure of the components, rigid travel stops on the force input lever of the construction, the specific mechanical advantage provided by the configuration of the device, and the hand strength of the user. Experience has shown that it is important to provide a consistent clamping force in an ultrasonic device in order to create the maximum tissue effect without overloading the system, again while providing good tactile feedback.

Commercial embodiments of the clamping apparatus disclosed in the above-referenced patent have included a reciprocable elongated wire-like element for transmitting movement from the operating lever of the device to the pivotal clamp arm of the clamping mechanism. It has been found that this arrangement inherently limits the force transmitted from the handle to the clamping mechanism. It is believed that the wire-like element is substantially unconfined along a substantial portion of its length, and due to the resilient flexibility of the wire-like element and associated elements and linkages, the device functions to limit force transmitted from the handle to the associated clamp arm. In particular, it is believed that the wire-like element is loaded in compression when driven to close the associated clamp arm. If excessive force is applied to the wire-like element, it is believed to deflect, in a column-like fashion, to limit the clamping force transmitted therethrough.

As will be recognized, variations in the grip strength of users of an ultrasonic clamp can result in large variations in the maximum clamping force which is applied to tissue at the end-effector. Excessive clamping force can cause overloading of the ultrasonic system, which can undesirably dampen the acoustic motion of the system and reduce the tissue effect. If a clamping mechanism is designed with a low mechanical advantage, to thereby limit the clamping force, some users may be fatigued quickly during use of the device, and experience difficulty in applying sufficient force at the operating lever to create sufficient clamping force at the end-effector. If clamping force is insufficient, the grasping capability of the instrument is undesirably limited, and the desired tissue effect may not be achieved.

Some previous ultrasonic clamp constructions formed from relatively stiff components exhibit desirable tactile feedback, but are not configured to limit clamping forces. In contrast, some devices have been constructed with components which can flex attendant to application of clamping force, which acts to limit clamping force, but does not provide the desired tactile feedback to the user due to the resultant "spongy" feel of the instrument. Such arrangements ordinarily are not configured to indicate when the maximum useable clamping force has been applied. As a consequence, a user may continue to apply additional force against a travel stop for the operating lever, not appreciating that additional clamping force is not being created, and creating user fatigue.

The present invention is directed to an ultrasonic clamp coagulator apparatus having a force-limiting clamp mechanism to limit the clamping force applied thereby, while still providing desirably good tactile feedback for a user.

SUMMARY OF THE INVENTION

An ultrasonic surgical clamp coagulator apparatus embodying the principles of the present invention is configured to permit selective cutting, coagulation, and clamping of tissue during surgical procedures. In order to desirably limit the force applied to tissue by the clamping mechanism, while maintaining good tactile feedback for a user, the clamp mechanism of the apparatus includes a force-limiting arrangement, including a pre-loaded spring. By virtue of the pre-loaded spring, the operating mechanism exhibits a desirably "stiff" and firm feel, thereby providing good tactile feedback and control over the clamping force. In the event that excessive force is applied to the operating mechanism by the user, components of the operating mechanism are movable relative to each other, in opposition to the pre-load spring. At least one travel stop is preferably provided for limiting movement of the operating lever prior to a predetermined degree of relative movement (in opposition to the pre-load spring) of the components of the operating mechanism.

In accordance with the illustrated embodiment, the present ultrasonic clamp coagulator apparatus includes a housing, and an outer tubular sheath having a proximal end rotatably joined to the housing. An inner, preferably tubular actuating member is reciprocably positioned within the outer tubular sheath for rotation therewith with respect to the apparatus housing. An ultrasonic waveguide is positioned within the outer tubular sheath, and includes an end-effector extending distally of a distal end of the outer tubular sheath.

Clamping of tissue against the end-effector is achieved by a clamp mechanism including a clamp arm pivotally mounted on the distal end of the outer tubular sheath of the apparatus. Pivotal movement of the clamp arm with respect to the end-effector permits tissue to be clamped therebetween. The clamp arm is operatively connected with the actuating member so that reciprocable movement of the actuating member pivotally moves the clamp arm with respect to the end-effector.

An operating lever is pivotally mounted on the housing, with the apparatus including a clamp drive mechanism operatively interconnecting the operating lever with the actuating member. By this construction, pivotal movement of the operating lever reciprocably moves the actuating member, thereby pivotally moving the clamp arm.

The clamp drive mechanism includes a drive collar joined to the actuating member, and a drive yoke which is operatively joined to the operating lever, and which engages the drive collar. Force transmitted from the operating lever to the clamp arm by the actuating member is limited by the provision of a pre-load spring which operatively interconnects the operating lever and the drive yoke. In particular, one of the operating lever and the drive yoke define a spring cage, with the other defining a spring slot positioned adjacent to the spring cage. A pre-load spring is held captive within the spring cage, and is positioned within the spring slot to thereby transmit and limit force transmitted from the operating lever to the drive yoke. In the preferred construction, the drive yoke and operating lever are mounted for pivotal movement about a common housing pivot, with relative pivotal movement of the drive yoke with respect to the operating lever taking place in opposition to the pre-load spring.

By this arrangement, the spring acts to pre-load the operative connection of the drive yoke and operating lever, with these components ordinarily pivoting as a unit with respect to their common housing pivot. However, in the event that excessive force is applied by a user to the operating lever, force transmitted to the clamp arm is limited by relative movement of the operating lever with respect to the drive yoke in opposition to the pre-load spring.

In the illustrated embodiment, the drive yoke defines the spring cage of the mechanism, with the operating lever preferably including a bifurcated portion having a pair of spring flanges, each defining a spring slot, positioned on respective opposite sides of the spring cage. The pre-load spring preferably comprises a compression coil spring positioned within the spring cage, as well as within the spring slots of the pair of spring flanges. The illustrated construction permits relative pivotal movement of the operating lever and drive yoke, in opposition to the coil spring, in either direction.

The clamp apparatus preferably includes a travel stop engageable by the operating lever prior to a predetermined degree of movement of the operating lever relative to the drive yoke. By this preferred arrangement, the operating lever engages the travel stop, thus preventing the input of any more clamping force into the clamp mechanism, prior to full compression of the coil spring of the force-limiting arrangement.

Other features and advantages of the present invention will become readily apparent from the following detailed description, the accompanying drawings, and the appended claims.

BRIEF DESCRIPTION OF THE DRAWINGS

FIG. 1 is a perspective view of an ultrasonic surgical system including an ultrasonic clamp coagulator apparatus embodying the principles of the present invention;

FIG. 2 is an enlarged, fragmentary perspective view of a clamp mechanism of the clamp coagulator apparatus illustrated in FIG. 1;

FIGS. 9–11 are diagrammatic views illustrating operation of the force-limiting arrangement of the clamp mechanism of the present invention.

DETAILED DESCRIPTION

Figure 3:
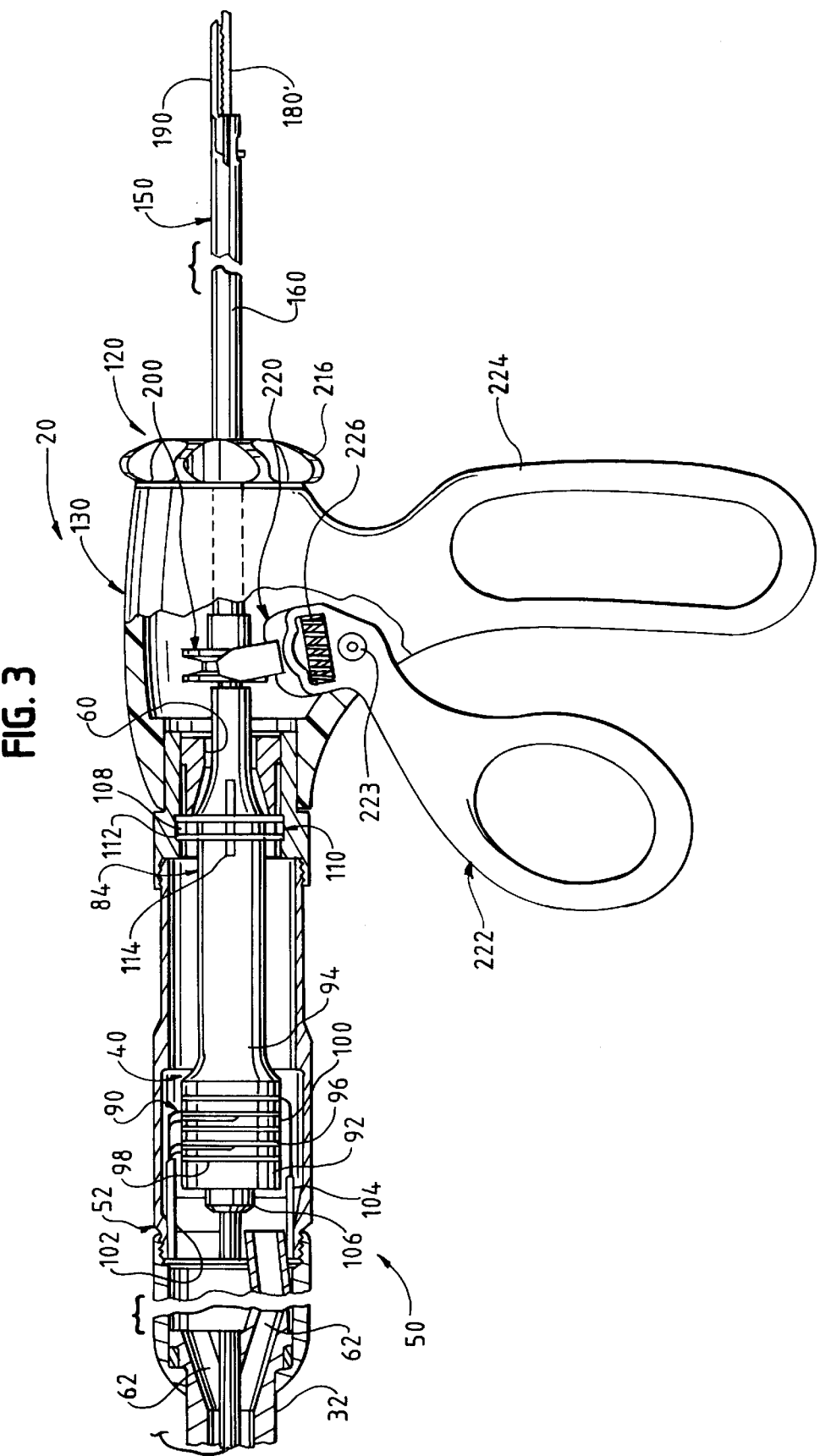
FIG. 3 is a side elevational view, partially in cut-away, of the clamp coagulator embodying the principles of the present invention, shown in operative association with an ultrasonic drive unit of the surgical system shown in FIG. 1.

While the present invention is susceptible of embodiments in various forms, there is shown in the drawings and will hereinafter be described a presently preferred embodiment, with the understanding that the present disclosure is to be considered as an exemplification of the invention, and is not intended to limit the invention to the specific embodiment illustrated.

The present invention is particularly directed to an improved ultrasonic surgical clamp coagulator apparatus which is configured for effecting tissue cutting, coagulation, and/or clamping during surgical procedures. The present apparatus can readily be configured for use in both open surgical procedures, as well as laparoscopic or endoscopic procedures. Versatile use is facilitated by selective use of ultrasonic energy. When ultrasonic components of the apparatus are inactive, tissue can be readily gripped and manipulated, as desired, without tissue cutting or damage. When the ultrasonic components are activated, the apparatus permits tissue to be gripped for coupling with the ultrasonic energy to effect tissue coagulation, with application of increased pressure efficiently effecting tissue cutting and coagulation. If desired, ultrasonic energy can be applied to tissue without use of the clamping mechanism of the apparatus by appropriate manipulation of the ultrasonic "blade" or end-effector of the device.

As will become apparent from the following description, the present clamp coagulator apparatus is particularly configured for disposable use by virtue of its straightforward construction. As such, it is contemplated that the apparatus be used in association with an ultrasonic drive unit of a surgical system, whereby ultrasonic energy from the drive unit provides the desired ultrasonic actuation of the present clamp coagulator apparatus. It will be appreciated that a clamp coagulator apparatus embodying the principles of the present invention can be configured for non-disposable use, and non-detachably integrated with an associated ultrasonic drive unit. However, detachable connection of the present clamp coagulator apparatus with an associated ultrasonic drive unit is presently preferred for single-patient use of the apparatus.

With reference first to FIGS. 1 and 3, therein is illustrated a presently preferred embodiment of a surgical system, generally designated 10, which includes an ultrasonic clamp coagulator apparatus embodying the principles of the present invention. Preferred details of the ultrasonic generator and associated ultrasonic drive unit of the surgical system 10 will first be described, with subsequent detailed description of the ultrasonic surgical clamp coagulator apparatus, including a clamp mechanism configured for indexed rotation, embodying the principles of the present invention.

The surgical system 10 includes an ultrasonic generator 30 and an associated ultrasonic surgical instrument. The surgical instrument includes an ultrasonic drive unit, designated 50, and an ultrasonic clamp coagulator apparatus 120 embodying the principles of the present invention. As will be further described, an ultrasonic transducer of the drive unit 50, and an ultrasonic waveguide of the clamp coagulator 120, together provide an acoustic assembly of the present surgical system, with the acoustic assembly providing ultrasonic energy for surgical procedures when powered by generator 30. It will be noted that in some applications, the ultrasonic drive unit 50 is referred to as a "hand piece assembly" because the surgical instrument of the surgical system is configured such that a surgeon grasps and manipulates the ultrasonic drive unit 50 during various procedures and operations. The clamp coagulator apparatus 120 embodying the principles of the present invention preferably includes a scissors-like grip arrangement which facilitates positioning and manipulation of the instrument apart from manipulation of the ultrasonic drive unit 50.

The generator 30 of the surgical system sends an electrical signal through a cable 32 at a selected excursion, frequency, and phase determined by a control system of the generator 30. As will be further described, the signal causes one or more piezoelectric elements of the acoustic assembly of the surgical instrument to expand and contract, thereby converting the electrical energy into mechanical motion. The mechanical motion results in longitudinal waves of ultrasonic energy that propagate through the acoustic assembly in an acoustic standing wave to vibrate the acoustic assembly at a selected frequency and excursion. An end-effector at the distal end of the waveguide of the acoustic assembly is placed in contact with tissue of the patient to transfer the ultrasonic energy to the tissue. As further described below, a surgical tool, such as, a jaw or clamping mechanism, is preferably utilized to press the tissue against the end-effector.

As the end-effector couples with the tissue, thermal energy or heat is generated as a result of friction, acoustic absorption, and viscous losses within the tissue. The heat is sufficient to break protein hydrogen bonds, causing the highly structured protein (i.e., collagen and muscle protein) to denature (i.e., become less organized). As the proteins are denatured, a sticky coagulum forms to seal or coagulate small blood vessels. Deep coagulation of larger blood vessels results when the effect is prolonged.

The transfer of the ultrasonic energy to the tissue causes other effects including mechanical tearing, cutting, cavitation, cell disruption, and emulsification. The amount of cutting as well as the degree of coagulation obtained varies with the excursion of the end-effector, the frequency of vibration, the amount of pressure applied by the user, the sharpness of the end-effector, and the coupling between the end-effector and the tissue.

As illustrated in FIG. 1, the generator 30 includes a control system integral with the generator 30, a power switch 34, and a triggering mechanism 36. The power switch 34 controls the electrical power to the generator 30, and when activated by the triggering mechanism 36, the generator 30 provides energy to drive the acoustic assembly of the surgical system 10 at a predetermined frequency and to drive the end-effector at a predetermined excursion level. The generator 30 drives or excites the acoustic assembly at any suitable resonant frequency of the acoustic assembly.

When the generator 30 is activated via the triggering mechanism 36, electrical energy is continuously applied by the generator 30 to a transducer stack or assembly 40 of the acoustic assembly. A phase-locked loop in the control system of the generator 30 monitors feedback from the acoustic assembly. The phase lock loop adjusts the frequency of the electrical energy sent by the generator 30 to match the resonant frequency of the selected longitudinal mode of vibration of the acoustic assembly including the tissue load. In addition, a second feedback loop in the control system maintains the electrical current supplied to the acoustic assembly at a preselected constant level in order to achieve substantially constant excursion at the end-effector of the acoustic assembly.

The electrical signal supplied to the acoustic assembly will cause the distal end of the waveguide, i.e., the end-effector, to vibrate longitudinally in the range of, for example, approximately 20 kHz to 250 kHz, and preferably in the range of about 54 kHz to 56 kHz, and most preferably at about 55.5 kHz. The excursion of the vibrations at the end-effector can be controlled by, for example, controlling the amplitude of the electrical signal applied to the transducer assembly 40 of the acoustic assembly by the generator 30.

As noted above, the triggering mechanism 36 of the generator 30 allows a user to activate the generator 30 so that electrical energy may be continuously supplied to the acoustic assembly. The triggering mechanism 36 preferably comprises a foot activating switch that is detachably coupled or attached to the generator 30 by a cable or cord. Alternatively, the triggering mechanism can be configured as a hand switch incorporated in the ultrasonic drive unit 50 to allow the generator 30 to be activated by a user.

The generator 30 also has a power line 38 for insertion in an electro-surgical unit or conventional electrical outlet. It is contemplated that the generator 30 can also be powered by a direct current (DC) source, such as a battery. The generator 30 can comprise any suitable generator, such as Model No. GEN01, available from Ethicon Endo-Surgery, Inc.

Referring to FIGS. 1 and 3, the ultrasonic drive unit 50 of the surgical instrument includes a multi-piece housing 52 adapted to isolate the operator from the vibrations of the acoustic assembly. The drive unit housing 52 can be shaped to be held by a user in a conventional manner, but it is contemplated that the present clamp coagulator 120 principally be grasped and manipulated by a scissors-like arrangement provided by a housing of the apparatus, as will be described. While the multi-piece housing 52 is illustrated, the housing 52 may comprise a single or unitary component.

The housing 52 of the ultrasonic drive unit 50 generally includes a proximal end, a distal end, and a cavity extending longitudinally therein. The distal end of the housing 52 includes an opening 60 configured to allow the acoustic assembly of the surgical system 10 to extend therethrough, and the proximal end of the housing 52 is coupled to the generator 30 by the cable 32. The cable 32 preferably includes ducts or vents 62 to allow air to be introduced into the housing 52 of the ultrasonic drive unit 50 to cool the transducer assembly 40 of the acoustic assembly.

The housing 52 of the ultrasonic drive unit 50 is preferably constructed from a durable plastic, such as Ultem®. It is also contemplated that the housing 52 may alternatively be made from a variety of materials including other plastics [i.e. liquid crystal polymer (LCP), nylon, or polycarbonate]. A suitable ultrasonic drive unit 50 is Model No. HP050, available from Ethicon Endo-Surgery, Inc.

The acoustic assembly of the surgical instrument generally includes a first acoustic portion and a second acoustic portion. The first acoustic portion is preferably carried by the ultrasonic drive unit 50, and the second acoustic portion (in the form of a waveguide and end-effector, as will be described) is carried by the ultrasonic clamp coagulator apparatus. The distal end of the first acoustic portion is operatively coupled to the proximal end of the second acoustic portion preferably by a threaded connection.

As shown in FIG. 3, the first acoustic portion includes the transducer stack or assembly 40 and a mounting device 84, and the second acoustic portion includes a transmission component or working member, referred to herein as a waveguide having an end-effector.

The components of the acoustic assembly are preferably acoustically tuned such that the length of each component is an integral number of one-half wavelengths ($n\lambda/2$), where the wavelength $\lambda$ is the wavelength of a preselected or operating longitudinal vibration frequency $f_o$ of the acoustic assembly, and n is any non-negative integer. It is also contemplated that the acoustic assembly may incorporate any suitable arrangement of acoustic elements.

The transducer assembly 40 of the acoustic assembly converts the electrical signal from the generator 30 into mechanical energy that results in longitudinal vibratory motion of the end-effector at ultrasonic frequencies. When the acoustic assembly is energized, a vibratory motion standing wave is generated through the acoustic assembly. The excursion of the vibratory motion at any point along the acoustic assembly depends on the location along the acoustic assembly at which the vibratory motion is measured. A minimum or zero crossing in the vibratory motion standing wave is generally referred to as a node (i.e., where motion is usually minimal), and an absolute value maximum or peak in the standing wave is generally referred to as an anti-node. The distance between an anti-node and its nearest node is one-quarter wavelength ($\lambda/4$).

As shown in FIG. 3, the transducer assembly 40 of the acoustic assembly, which is also known as a "Langevin stack", generally includes a transduction portion 90, a first resonator 92, and a second resonator 94. The transducer assembly is preferably an integral number of one-half system wavelengths ($n\lambda/2$) in length. It is to be understood that the present invention may be alternatively configured to include a transducer assembly comprising a magnetostrictive, electromagnetic or electrostatic transducer.

The distal end of the first resonator 92 is connected to the proximal end of transduction section 90, and the proximal end of the second resonator 94 is connected to the distal end of transduction portion 90. The first and second resonators 92 and 94 are preferably fabricated from titanium, aluminum, steel, or any other suitable material, and most preferably, the first resonator 92 is fabricated from 303 stainless steel and the second resonator 94 is fabricated from 7075-T651 Aluminum. The first and second resonators 92 and 94 have a length determined by a number of variables, including the length of the transduction section 90, the speed of sound of material used in the resonators 92 and 94, and the desired fundamental frequency $f_o$ of the transducer assembly 40. The second resonator 94 can be tapered inwardly from its proximal end to its distal end to function as a velocity transformer and amplify the ultrasonic vibration excursion.

The transduction portion 90 of the transducer assembly 40 preferably comprises a piezoelectric section of alternating positive electrodes 96 and negative electrodes 98, with piezoelectric elements 100 alternating between the electrodes 96 and 98. The piezoelectric elements 100 can be fabricated from any suitable material, such as, for example, lead zirconate-titanate, lead metaniobate, lead titanate, or other piezoelectric material. Each of the positive electrodes 96, negative electrodes 98, and piezoelectric elements 100 have a bore extending through the center. The positive and negative electrodes 96 and 98 are electrically coupled to wires 102 and 104, respectfully. The wires 102 and 104 transmit the electrical signal from the generator 30 to electrodes 96 and 98.

As illustrated in FIG. 3, the piezoelectric elements 100 are held in compression between the first and second resonators 92 and 94 by a bolt 106. The bolt 106 preferably has a head, a shank, and a threaded distal end. The bolt 106 is inserted from the proximal end of the first resonator 92 through the bores of the first resonator 92, the electrodes 96 and 98, and piezoelectric elements 100. The threaded distal end of the bolt 106 is screwed into a threaded bore in the proximal end of second resonator 94. The bolt can be fabricated from steel, titanium, aluminum, or other suitable material and is preferably fabricated from Ti-6A1-4V Titanium, and most preferably from 4037 low alloy steel.

The piezoelectric elements 100 are energized in response to the electrical signal supplied from the generator 30 to produce an acoustic standing wave in the acoustic assembly. The electrical signal causes an electromagnetic field across the piezoelectric elements 100, causing the piezoelectric elements 100 to expand and contract in a continuous manner along the axis of the voltage gradient, producing high frequency longitudinal waves of ultrasonic energy. The ultrasonic energy is transmitted through the acoustic assembly to the end-effector.

The mounting device 84 of the acoustic assembly has a proximal end, a distal end, and preferably has a length substantially equal to an integral number of one-half system wavelengths. The proximal end of the mounting device 84 is preferably axially aligned and coupled to the distal end of the second resonator 94 by an internal threaded connection near an anti-node. (For purposes of this disclosure, the term "near" is defined as "exactly at" or "in close proximity to".) It is also contemplated that the mounting device 84 may be attached to the second resonator 94 by any suitable means, and the second resonator 94 and mounting device 84 may be formed as a single or unitary component.

The mounting device 84 is coupled to the housing 52 of the ultrasonic drive unit 50 near a node. The mounting device 84 preferably includes an integral mounting flange 108 disposed around its periphery. The mounting flange 108 is preferably disposed in an annular groove 110 formed in the housing 52 of the ultrasonic drive unit 50 to couple the mounting device 84 to the housing 52. A compliant member or material 112, such as a pair of silicone rubber O-rings attached by stand-offs, may be placed between the annular groove 110 of the housing 52 and the integral flange 108 of the mounting device 86 to reduce or prevent ultrasonic vibration from being transmitted from the mounting device 84 to the housing 52.

The mounting device 84 is preferably secured in a predetermined axial position by a plurality of pins 114, preferably four. The pins 114 are disposed in a longitudinal direction ninety (90) degrees apart from each other around the outer periphery of the mounting device 84. The pins 114 are coupled to the housing 52 of the ultrasonic drive unit 50 and are disposed through notches in the acoustic mounting flange 108 of the mounting device 84. The pins 114 are preferably fabricated from stainless steel.

The mounting device 84 is preferably configured to amplify the ultrasonic vibration excursion that is transmitted through the acoustic assembly to the distal end of the end-effector. In one preferred embodiment, the mounting device 84 comprises a solid, tapered horn. As ultrasonic energy is transmitted through the mounting device 84, the velocity of the acoustic wave transmitted through the mounting device 84 is amplified. It is contemplated that the mounting device 84 be configured as any suitable shape, such as, for example, a stepped horn, a conical horn, an exponential horn, a unitary gain horn, or the like.

As shown in FIG. 3, the mounting device 84 is preferably acoustically coupled to the second acoustic portion of the ultrasonic clamp coagulator apparatus 120. The distal end of the mounting device 84 is preferably coupled to the proximal end of the second acoustic portion by an internal threaded connection near an anti-node, but alternative coupling arrangements can be employed.

Figure 4:
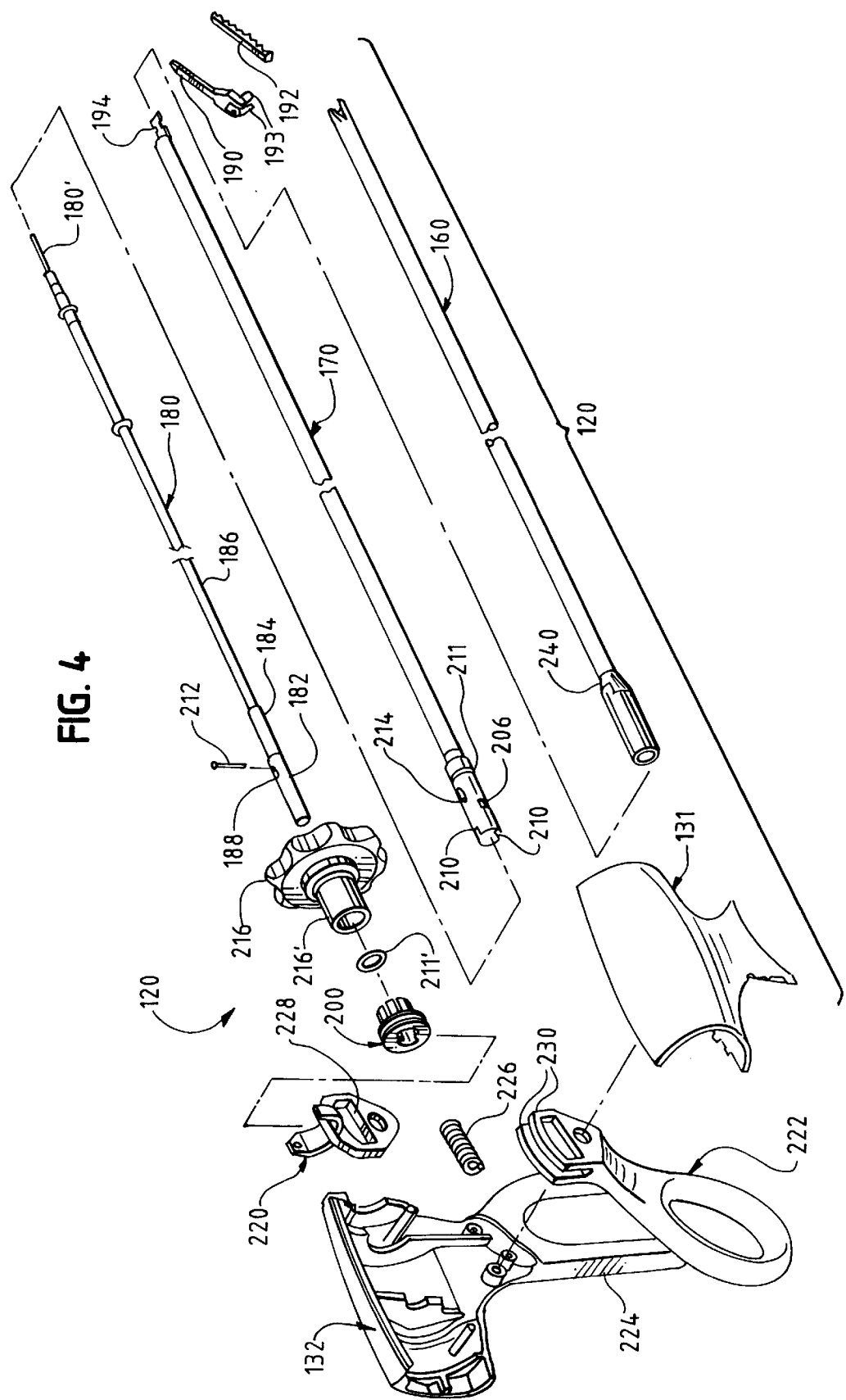
FIG. 4 is an exploded view of the ultrasonic surgical clamp coagulator apparatus embodying the principles of the present invention.

Referring now to FIG. 4, an exploded view of the ultrasonic clamp coagulator apparatus 120 of the surgical system 10 in accordance with a preferred embodiment is illustrated. The proximal end of the ultrasonic clamp coagulator apparatus 120 preferably receives and is fitted to the distal end of the ultrasonic drive unit 50 by insertion of the drive unit into the housing of the apparatus, as shown in FIG. 3. The ultrasonic clamp coagulator apparatus 120 is preferably attached to and removed from the ultrasonic drive unit 50 as a unit. The ultrasonic clamp coagulator 120 may be disposed of after a single use.

The ultrasonic clamp coagulator apparatus 120 preferably includes a handle assembly or a housing 130, preferably comprising mating housing portions 131, 132, and an elongated or endoscopic portion 150. When the present apparatus is configured for endoscopic use, the construction can be dimensioned such that portion 150 has an outside diameter of about 5.5 mm. The elongated portion 150 of the ultrasonic clamp coagulator apparatus 120 extends orthogonally from the apparatus housing 130. The elongated portion 150 can be selectively rotated with respect to the housing 130 as further described below. The elongated portion 150 preferably includes an outer tubular member or sheath 160, an inner tubular actuating member 170, and the second acoustic portion of the acoustic system in the form of a waveguide 180 having an end-effector 180'. As will be described, the outer sheath 160, the actuating member 170, and the waveguide 180 are preferably joined together for indexed rotation as a unit (together with ultrasonic drive unit 50) relative to housing 130.

As illustrated in FIG. 4, the proximal end of the waveguide 180 of the second acoustic portion is preferably detachably coupled to the mounting device 84 of the ultrasonic drive unit 50 near an anti-node as described above. The waveguide 180 preferably has a length substantially equal to an integer number of one-half system wavelengths (nλ/2). The waveguide 180 is preferably fabricated from a solid core shaft constructed out of material which propagates ultrasonic energy efficiently, such as titanium alloy (i.e., Ti-6Al-4V) or an aluminum alloy. It is contemplated that the waveguide 180 can alternatively be fabricated from any other suitable material.

The waveguide is preferably substantially semi-flexible. It will be recognized that the waveguide can alternatively be substantially rigid or may comprise a flexible wire. The waveguide may be configured to amplify the mechanical vibrations transmitted through the waveguide to the end-effector as is well known in the art. The waveguide may further have features to control the gain of the longitudinal vibration along the waveguide and features to tune the waveguide to the resonant frequency of the system.

It will be recognized that the waveguide 180 may have any suitable cross-sectional dimension. For example, the waveguide may have a substantially uniform cross-section or the waveguide may be tapered at various sections or may be tapered along its entire length.

As shown in FIG. 4, the waveguide 180 generally has a first section 182, a second section 184, and a third section 186. The first section 182 of the waveguide extends distally from the proximal end of the waveguide, and has a substantially continuous cross-section dimension.

The first section 182 preferably includes at least one radial hole or aperture 188 extending diametrically therethrough, substantially perpendicular to the axis of the waveguide 180. The aperture 188 is preferably positioned at a node, but may be otherwise positioned. It will be recognized that the aperture 188 may have any suitable depth and may be any suitable shape. The aperture is configured to receive a connector pin member which connects the waveguide 180, the tubular actuating member 170, and the tubular outer sheath 160 together for conjoint, indexed rotation relative to apparatus housing 130.

The second section 184 of the waveguide 180 extends distally from the first section 182. The second section 184 preferably also has a substantially continuous cross-section. The diameter of the second section 184 is smaller than the diameter of the first section 182 and larger than the diameter of the third section 186. As ultrasonic energy passes from the first section 182 of the waveguide 180 into the second section 184, the narrowing of the second section 184 will result in an increased amplitude of the ultrasonic energy passing therethrough.

The third section 186 extends distally from the distal end of the second section 184. The third section 186 also has a substantially continuous cross-section. The third section 186 may also include small diameter changes along its length. As ultrasonic energy passes from the second section 184 of the waveguide 180 into the third section 186, the narrowing of the third section 186 will result in an increased amplitude of the ultrasonic energy passing therethrough.

The third section 186 may have a plurality of grooves or notches (not shown) formed in its outer circumference. The grooves may be located at nodes of the waveguide 180 to act as alignment indicators for the installation of a damping sheath (not shown) and stabilizing silicone rings or compliant supports during manufacturing. A seal is preferably provided at the distal-most node, nearest the end-effector 180', to abate passage of tissue, blood, and other material in the region between the waveguide and actuating member 170.

The end-effector 180' of the waveguide 180 is preferably integral therewith and formed as a single unit. The end-effector may alternately be connected by a threaded connection, or by a welded joint. The distal end of the end-effector is disposed near an anti-node in order to tune the acoustic assembly to a preferred resonant frequency $f_0$ when the acoustic assembly is not loaded by tissue. When the transducer assembly is energized, the distal end of the end-effector is configured to move longitudinally in the range of, for example, approximately 10–500 microns peak-to-peak, and preferably in the range of about 10 to about 100 microns at a predetermined vibrational frequency $f_0$.

In accordance with the illustrated embodiment, the end-effector 180', sometimes referred to as a blade, is preferably cylindrical for cooperation with the associated clamping mechanism of the present clamp coagulator apparatus. The end-effector may receive suitable surface treatment, as is known in the art.

With particular reference to FIG. 2, therein is illustrated the clamping mechanism of the present clamp coagulator 120, which is configured for cooperative action with the end-effector 180' of the waveguide 180. The clamping mechanism includes a pivotally movable clamp arm 190, which is pivotally connected at the distal end thereof to the distal end of outer tubular sheath 160. A clamp pad 192, preferably formed from Teflon or other suitable low-friction material, is mounted on the surface of the clamp arm for cooperation with the end-effector 180', with pivotal movement of the clamp arm positioning the clamp pad in substantially parallel relationship to, and in contact with, the end-effector 180'. By this construction, tissue to be clamped is grasped between the pad 192 and the end effector 180'. As illustrated, the pad 192 is preferably provided with a sawtooth-like configuration to enhance the gripping of tissue in cooperation with the end-effector 180'.

Pivotal movement of the clamp arm with respect to the end-effector is effected by the provision of at least one, and preferably a pair of lever portions 193 of the clamp arm 190 at the proximal end thereof. The lever portions are positioned on respective opposite sides of the waveguide 180 and end-effector 180', and are in operative engagement with a drive portion 194 of the reciprocable actuating member 170. Reciprocable movement of the actuating member, relative to the outer tubular sheath 160 and the waveguide 180, thereby effects pivotal movement of the clamp arm relative to the end-effector. The lever portions 193 can be respectively positioned in a pair of openings defined by the drive portion 194, or otherwise suitably mechanically coupled therewith, whereby reciprocable movement of the actuating member acts through the drive portion 194 and lever portions 193 to pivot the clamp arm.

Figure 5:
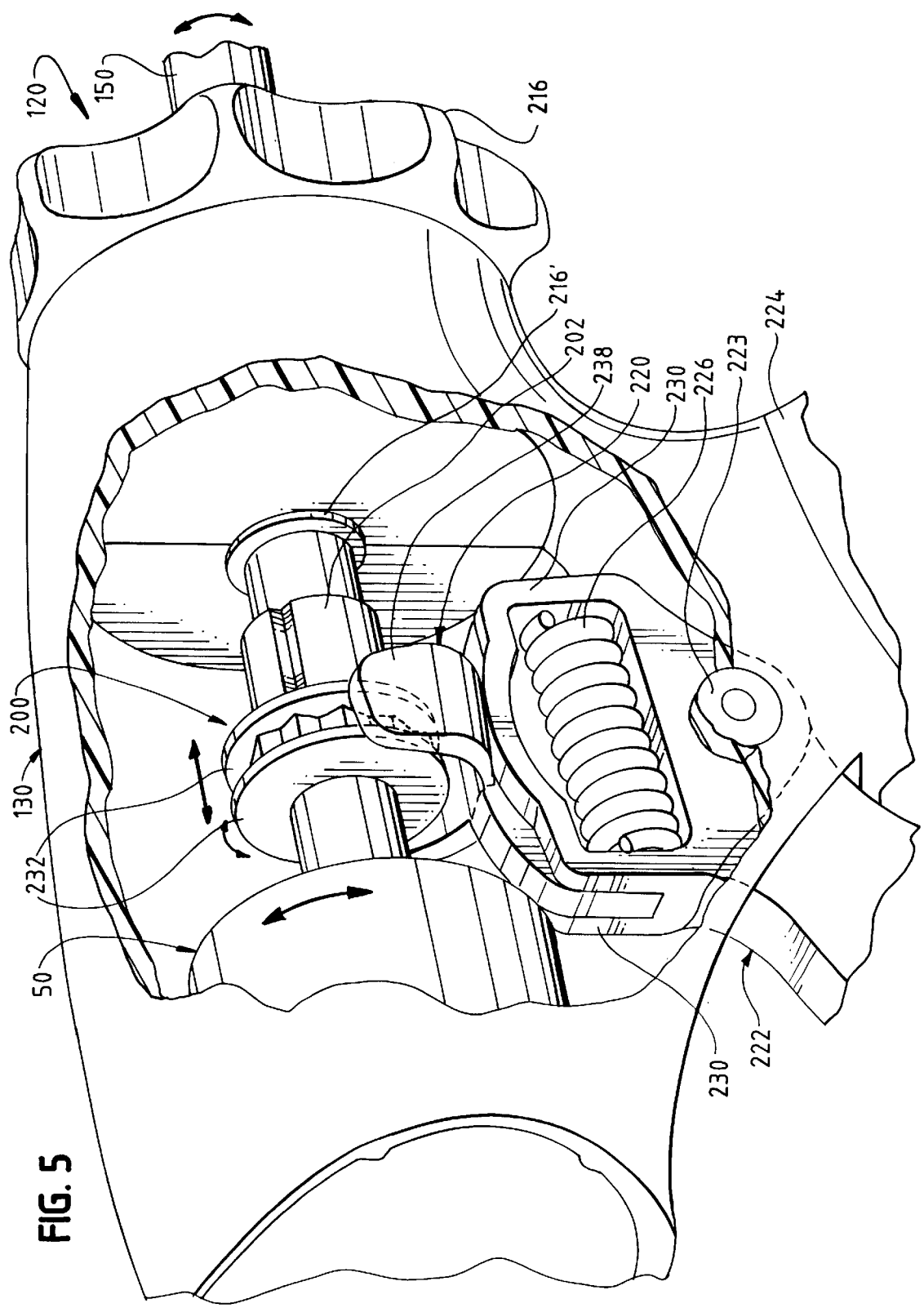
FIG. 5 is an enlarged, fragmentary view of the present clamp coagulator apparatus illustrating a clamp drive mechanism thereof and associated detent mechanism.
Figure 6:
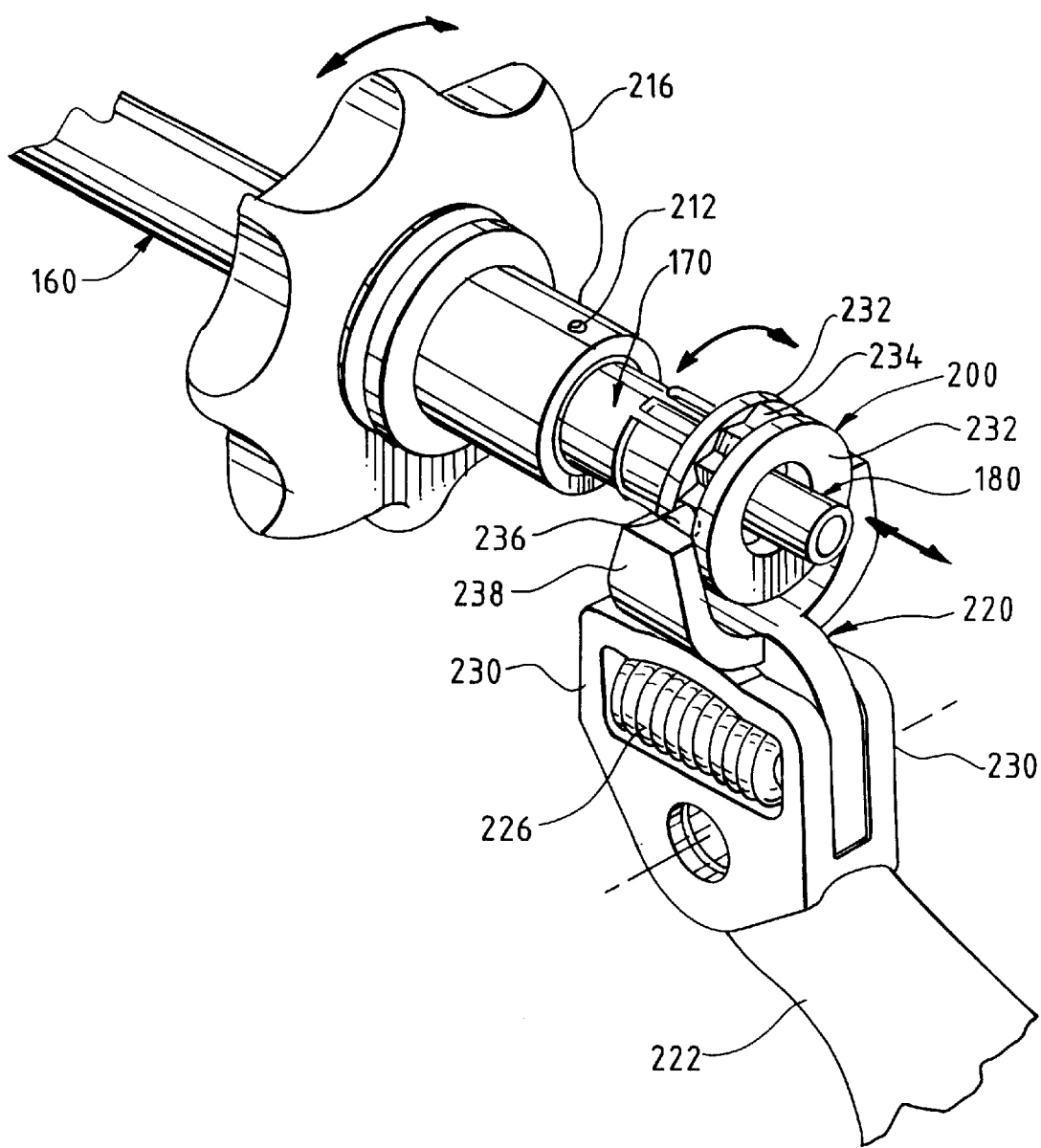
FIG. 6 is a diagrammatic view further illustrating the clamp drive mechanism and detent mechanism of the present clamp coagulator apparatus.
Figure 7:
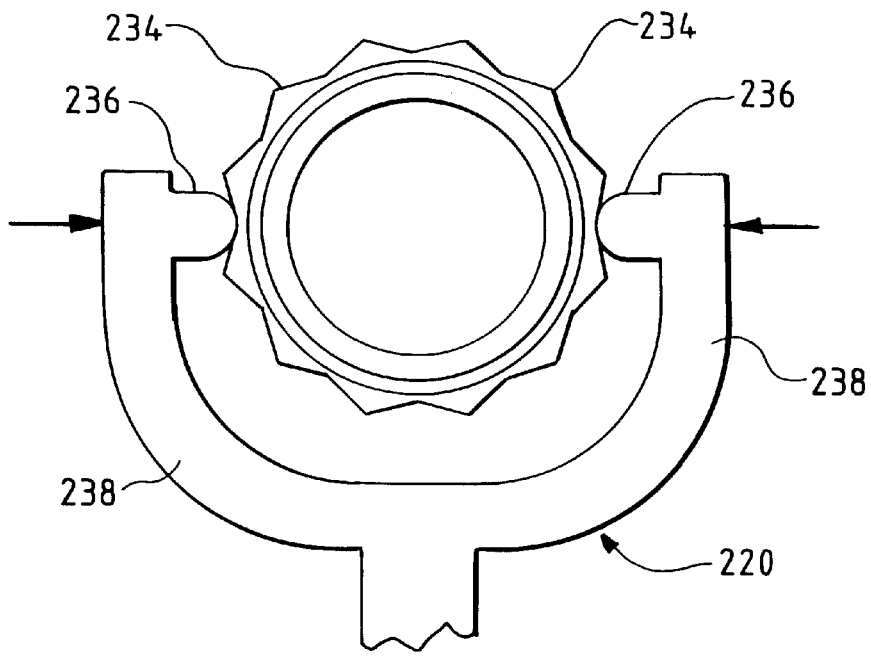
FIG. 7 is a diagrammatic view of the detent mechanism of the present invention.
Figure 8:
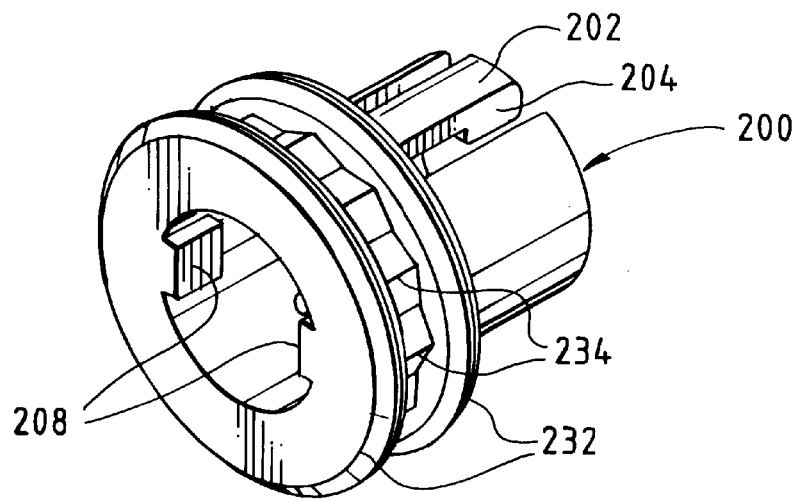
FIG. 8 is a perspective view of a clamp mechanism drive collar of the present clamp coagulator apparatus.

With particular reference to FIGS. 3, 5, and 6, reciprocable movement of the actuating member 170 is effected by the provision of a drive collar, generally designated 200, mounted on the proximal end of the actuating member for conjoint rotation. To this end, the drive collar includes a pair of diametrically opposed axially extending arms 202 each having a drive lug 204, with the drive lugs being biased by the arms 202 into engagement with suitable openings 206 defined by the proximal portion of tubular actuating member 170. Rotation of the drive collar 200 together with the actuating member 170 is further effected by the provision of a pair of keys 208 (see FIG. 8) diametrically engageable with suitable openings 210 defined by the proximal end of the actuating member 170. A circumferential groove 211 on the actuating member 170 receives on O-ring 211' (FIG. 4) for engagement with the inside surface of outer sheath 160.

Rotation of the actuating member 170 together with tubular outer sheath 160 and inner waveguide 180 is provided by a connector pin 212 extending through these components of the apparatus. As illustrated in FIG. 4, the tubular actuating member 170 defines an elongated slot 214 through which the connector pin 212 extends to accommodate reciprocable movement of the actuating member relative to the outer tubular sheath and inner waveguide.

A rotation knob 216 mounted on the outer tubular sheath facilitates rotational positioning of the elongated portion 150 with respect to the housing 130 of the clamp coagulator apparatus. Connector pin 212 preferably joins knob 216 together with sheath 160, member 170, and waveguide 180 for rotation as a unit relative to housing 130. In a current embodiment, hub portion 216' of the rotation knob acts to rotatably mount the outer sheath 160, the actuating member 170, and the waveguide 180 (as a unit with knob 216), on the housing 130.

In accordance with the present invention, the drive collar 200 provides a portion of the clamp drive mechanism of the apparatus which effects pivotal movement of the clamp arm 190 by reciprocation of actuating member 170. The clamp drive mechanism further includes a drive yoke 220 which is operatively connected with an operating lever 222 of the apparatus, with the operating lever thus interconnected with the reciprocable actuating member 170 via drive yoke 220 and drive collar 200. The operating lever 222 is pivotally connected to the housing 130 of the apparatus (by a pivot mount 223) for cooperation in a scissors-like fashion with a handgrip portion 224 of the housing. Movement of lever 222 toward handgrip portion 224 translates actuating member 170 proximally, thereby pivoting clamp arm 190 toward end-effector 180'.

The drive yoke 220 is operatively connected with operating lever 222 so that these components are normally pivotally movable, as a unit, about a common pivot mount 223 of housing 130. In accordance with the present invention, force transmitted from the operating lever to the drive yoke is limited by an arrangement which permits relative movement therebetween in opposition to a force-limiting spring. The force-limiting spring, designated 226, preferably comprises a compression coil spring which is arranged to operatively connect the drive yoke 220 with the operating lever 222. Specifically, the drive yoke 220 includes a spring cage which defines a spring slot 228 within which spring 226 is positioned in a pre-loaded condition. The operative connection of the operating lever and the drive yoke further comprises at least one, and preferably a pair, of spring retainer flanges 230 positioned on respective opposite sides of the spring cage (and spring slot 228) of drive yoke 220. The spring slot 228 is thus positioned between the spring flanges 238 of this bifurcated portion of the operating lever, with the pre-loaded spring 226 being held captive within the spring slot 228 defined by the drive yoke, and extending laterally thereof for positioning within openings respectively defined by the spring flanges 238. Thus, each spring flange is positioned adjacent to the spring cage of the drive yoke 220, with the spring positioned within the spring cage further being positioned within each spring slot as defined by each spring flange 238.

As noted, the drive yoke 220 and operating lever 222 ordinarily are pivotally movable as a unit with respect to pivot mount 23 of housing 130. However, the present force-limiting arrangement is configured such that the drive yoke 220 is pivotally movable with respect to spring flanges 230 (about pivot mount 223) in opposition to the spring 226. This arrangement is achieved by having the spring bear against the surfaces of the spring slots defined by each of the spring flanges 230, as the spring is held captive within the spring cage of the drive yoke. By this arrangement, force which is applied to the reciprocable actuating member 170 of the apparatus, by pivotal movement of operating lever 222 acting through drive yoke 220 and drive collar 200, is limited by the force with which spring 226 bears against the spring flanges 230. Application of excessive force results in pivotal displacement of spring flanges 230 of the operating lever relative to drive yoke 220 in opposition to spring 226. When the force which is applied exceeds the pre-load limit of the spring 226, the operating lever 222 is pivotally movable with respect to the drive yoke 220, in opposition to the spring. The operating lever can thus move independently from the drive yoke for a limited degree.

In a presently preferred embodiment, the spring rate of spring 226 is selected to provide a clamping force, between clamp arm 190 and end-effector 180', of preferably between about 1 pound and about 3.5 pounds, measured at the middle of the clamp arm 190, and most preferably between about 2 pounds and 2.5 pounds. It will be appreciated that different shapes of the end-effector 180' and the clamp arm 190 can dictate different operating ranges for optimal clamping forces, and that different excursions or frequency of operation may also mandate different clamping force ranges.

As will be recognized, it can be desirable to limit the relative movement between drive yoke 220 and operating lever 222 to avoid full compression of spring 226. To this end, the housing 130 of the apparatus preferably includes at least one travel stop for operative engagement with the operating lever 222, to thereby limit relative movement between the operating lever 222 and drive yoke 220. As shown in FIGS. 9, 10, and 11, housing portion 132 of the housing 130 includes a travel stop 232 which is engageable with the operating lever 222 after a predetermined degree of movement of operating lever 222 relative to drive yoke 220. It is presently preferred that an additional travel stop (not numbered) be provided on the apparatus housing for limiting movement of operating lever 222 with respect to the drive yoke in an opposite direction, that is, in a direction in which lever 222 is moved away from hand grip portion 224.

With further reference to FIGS. 9, 10, and 11, operation of the present force-limiting clamping mechanism is illustrated. As shown in FIG. 9, the present apparatus is illustrated in a configuration prior to operation of the clamping mechanism. As will be observed, a dimension $D_1$ shows the spacing between drive collar 220 and the associated rotation knob 216 fitted to the outside of outer tubular sheath 160.

FIG. 10 illustrates the position of operating lever 222 after the clamping mechanism has been moved through its maximum stroke, but prior to relative movement of lever 222 relative to drive yoke 220. As will be observed, dimension $D_2$ shows that the actuating member (170) to which drive collar 220 is fixed has been withdrawn relative to rotation knob 216 and the outer tubular sheath of the apparatus (thus closing clamp arm 190). In this condition of the apparatus, operating lever 222 is spaced from hand grip portion 224 by a dimension $S_1$, with the lever 222 spaced from travel stop 232.

Having reached the maximum displacement of drive collar 200 and actuating member 170 with respect to rotation knob 216 and outer tubular sheath 160, i.e., dimension $D_2$, application of further force to operate lever 222 results in pivotal movement of the operating lever with respect to drive yoke 220, in opposition to spring 226. As will be observed, operating lever 222 has moved to a relatively closer spacing to hand grip 224, dimension $S_2$, with FIG. 11 illustrating that the operating lever has moved with respect to drive yoke 220. By virtue of this relative movement, in opposition to spring 226, minimal additional force is applied to drive collar 200 and actuating member 170.

FIG. 11 further illustrates engagement of operating lever 222 with travel stop 232. Input of any additional force into the operating lever 222 will not act to further relatively move the operating lever with respect to drive yoke 220 (in opposition to spring 226). Thus, only a predetermined degree of relative movement is permitted between the operating lever 222 and drive yoke 220 before the operating lever engages the travel stop 232. As noted, a similar limitation in the degree of relative movement of these components is preferably achieved by the provision of another travel stop, on the housing 130 generally at the rearward surface of operating lever 222, thus limiting relative displacement of the components when the operating lever 222 is moved in a direction to open clamp arm 190.

Thus, the clamp mechanism of the present apparatus includes a force-limiting arrangement provided by the operative connection of operating lever 222 and spring yoke 220 by spring 226. The spring 226 is preferably pre-loaded in position within the spring cage of the drive yoke, and the associated spring slots of the spring flanges 238, thus ordinarily joining these components, under the influence of the spring pre-load, to provide a relatively "stiff" connection therebetween. By virtue of this relatively stiff connection, a user of the apparatus is afforded good tactile feedback as the clamp arm 190 of the apparatus is pivotally moved by manipulation of the operating lever. In the event that excessive force is applied to the operating lever, the operating lever is pivotally displaced with respect to the drive yoke, in opposition to spring 226. As described, operating lever 222 is engageable with travel stop 232 on the apparatus housing prior to full compression of the coil spring preferably provided in the drive mechanism. Notably, such relative displacement of the operating lever and drive yoke, and subsequent engagement with the travel stop, is readily tactilely discernable by a user, thus signaling that maximum clamping force has been achieved.

Indexed rotational positioning of the elongated portion 150 of the present clamp coagulator apparatus 120 is provided by the provision of a detent mechanism incorporated into the clamp drive mechanism of the apparatus. Specifically, the drive collar 200 includes a pair of axially spaced apart drive flanges 232. A detent-receiving surface is provided between the drive flanges 232, and defines a plurality of circumferentially spaced teeth 234 which define detent-receiving depressions generally about the periphery of the drive collar 200. In a presently preferred embodiment, twelve (12) of the teeth 234 are provided, thereby providing indexed positioning of the elongated portion 150 of the apparatus at 30° intervals relative to the housing 130 of the apparatus.

Indexed rotational movement is further achieved by the provision of at least one, and preferably a pair, of diametrically opposed detents 236 respectively provided on cantilevered yoke arms 238 of drive yoke 220. By this arrangement, the yoke arms 238 are positioned between the drive flanges 232 for engagement with the confronting surfaces thereof, and bias the detents 236 into engagement with the drive collar 200. Indexed relative rotation is thus achieved, with the detents 236 of the yoke arms cooperating with the drive flanges 238 for effecting reciprocation of the actuating member 170. In a presently preferred embodiment, the drive yoke 220 is formed from suitable polymeric material, with the biasing force created by the yoke arms acting on the detents thereof cooperating with the radial depressions defined by the drive collar to resist relative rotational torque less than about 5 to 20 inch-ounces. As such, the elongated portion 150 of the clamp coagulator apparatus is maintained in any of its selected indexed rotational positions, relative to housing 130, unless a torque is applied (such as by rotation knob 216) exceeding this predetermined torque level. A snap-like indexing action is thus provided.

Rotation of the elongated proportion 150 of the present clamp coagulator apparatus 120 is preferably effected together with relative rotational movement of ultrasonic drive unit 50 with respect to apparatus housing 130. In order to join the elongated portion 150 to the ultrasonic drive unit 50 in ultrasonic-transmitting relationship, the proximal portion of the outer tubular sheath 160 is preferably provided with a pair of wrench flats 240 (see FIG. 4). The wrench flats allow torque to be applied by a suitable torque wrench or the like to thereby permit the waveguide 180 to be joined to the ultrasonic drive unit 50. The ultrasonic drive unit, as well as the elongated portion 150, are thus rotatable, as a unit, by suitable manipulation of rotation knob 216, relative to housing 130 of the apparatus. The interior of housing 130 is dimensioned to accommodate such relative rotation of the drive unit 50.

Thus, the present surgical clamp coagulator apparatus is configured for highly efficient and versatile use, with the construction being sufficiently straight-forward and economical in configuration to permit single-patient use. Components of the apparatus can be fabricated from materials suited for surgical applications. By virtue of the detent mechanism provided by cooperation of drive collar 200 and drive yoke 220, selective angular positioning of the elongated portion 150 of the apparatus, and the associated ultrasonic drive unit 50, is readily effected with respect to the housing 130 of the apparatus. The scissors-like action provided by pivotal operating lever 222 and cooperating handgrip portion 224 facilitates convenient and efficient manipulation and positioning of the apparatus, and operation of the clamping mechanism at the distal portion of the apparatus whereby tissue is efficiently urged against the end-effector 180'. The detent mechanism resists rotation of the ultrasonic drive unit, and associated cable assembly, with respect to the housing 130 with the resistence to rotation readily and conveniently overcome by application of sufficient torque via rotation knob 216.

From the foregoing, it will be observed that numerous modifications and variations can be effected without departing from the true spirit and scope of the novel concept of the present invention. It is to be understood that no limitation with respect to the specific embodiment illustrated herein is intended or should be inferred. The disclosure is intended to cover, by the appended claims, all such modifications as fall within the scope of the claims.

What is claimed is:

1. An ultrasonic surgical clamp apparatus comprising:

a housing;

an outer tubular sheath having a proximal end joined to said housing, and a distal end;

an inner actuating member reciprocably positioned within said outer tubular sheath;

an ultrasonic waveguide positioned within said outer tubular sheath and having an end-effector extending distally of said distal end of said outer tubular sheath;

a clamp arm pivotally mounted on said distal end of said outer tubular sheath for pivotal movement with respect to said end-effector for clamping tissue between said clamp arm and said end-effector, said clamp arm being operatively connected to said actuating member so that reciprocable movement of said actuating member pivotally moves said clamp arm with respect to said end-effector;

an operating lever pivotally mounted on said housing for pivotal movement relative to a lever pivot axis, and a clamp drive mechanism interconnecting said operating lever with said actuating member so that pivotal movement of said operating lever reciprocably moves said actuating member for pivotally moving said clamp arm, said clamp drive mechanism including a reciprocably movable drive collar joined to said actuating member for reciprocable movement therewith relative to said outer tubular sheath, and a drive yoke operatively joined to said operating lever for movement relative to said lever pivot axis, said drive yoke engaging said drive collar so that pivotal movement of said operating lever and said drive yoke reciprocably moves said drive collar and said inner actuating member, one of said operating lever and said drive yoke defining a spring cage, and the other defining a spring slot positioned adjacent to said spring cage, with a spring held captive within said spring cage positioned within said spring slot to transmit and limit force transmitted from said operating lever to said drive yoke by movement of said operating lever relative to said drive yoke in opposition to said spring.

2. An ultrasonic clamp apparatus in accordance with claim 1, wherein said operating lever includes a bifurcated portion having a pair of spring flanges each defining one of said spring slots, said spring cage being provided on said drive yoke and being positioned between said pair of spring flanges.

3. An ultrasonic clamp apparatus in accordance with claim 1, wherein said housing includes at least one travel stop to limit pivotal movement of said operating lever relative to said housing.

4. An ultrasonic clamp apparatus in accordance with claim 1, wherein said spring comprises a compression coil spring.

5. An ultrasonic surgical clamp apparatus comprising:

a housing;

an outer tubular sheath having a proximal end rotatably joined to said housing, and a distal end;

a rotation knob mounted on said outer sheath for effecting rotation thereof with respect to said housing;

an inner tubular actuating member reciprocably positioned within said outer tubular sheath for rotation therewith with respect to said housing;

an ultrasonic waveguide positioned within said outer tubular sheath and having an end-effector extending distally of said distal end of said outer tubular sheath;

a clamp arm pivotally mounted on said distal end of said outer tubular sheath for pivotal movement with respect to said end-effector for clamping tissue between said clamp arm and said end-effector, said clamp arm being operatively connected to said actuating member so that reciprocable movement of said actuating member pivotally moves said clamp arm with respect to said end-effector;

an operating lever pivotally mounted on said housing on a housing pivot, and a clamp drive mechanism interconnecting said operating lever with said actuating member so that pivotal movement of said operating lever reciprocably moves said actuating member for pivotally moving said clamp arm;

said clamp drive mechanism including a reciprocably movable drive collar joined to said actuating member for conjoint rotation and for reciprocable movement therewith relative to said outer tubular sheath, and a drive yoke operatively joined to said operating lever which engages said drive collar while permitting relative rotation therebetween, said drive yoke being pivoted about said housing pivot to reciprocably move said drive collar and said actuating member, a force-limiting spring operatively interconnecting said drive yoke and said operating lever to limit force transmitted therebetween by movement of said operating lever relative to said drive yoke in opposition to said force-limiting spring, said housing including a travel stop engageable by said operating lever after a predetermined degree of movement of said operating lever relative to said drive yoke.

6. An ultrasonic clamp apparatus in accordance with claim 5, wherein said spring comprises a compression coil spring, said operating lever being engageable with said travel stop prior to full compression of said coil spring.

7. An ultrasonic clamp apparatus in accordance with claim 5, wherein said drive yoke includes a spring cage within which said spring is positioned, said operating lever including at least one spring flange positioned adjacent to said spring cage and defining a spring slot within which said spring is further positioned.

8. An ultrasonic clamp apparatus in accordance with claim 7, wherein said operating lever includes a bifurcated portion having a pair of said spring flanges positioned adjacent to and on respective opposite sides of said spring cage, said spring being positioned with a spring slot defined by each of said spring flanges.

\* \* \* \* \*